United States Patent
Winge

(12) 
(10) Patent No.: US 6,451,978 B2
(45) Date of Patent: Sep. 17, 2002

(54) PURIFICATION OF ANTITHROMBIN-III-α AND β

(75) Inventor: Stefan Winge, Årsta (SE)

(73) Assignee: Biovitrum AB, Stockholm (SE)

(*) Notice: Subject to any disclaimer, the term of this patent is extended or adjusted under 35 U.S.C. 154(b) by 0 days.

(21) Appl. No.: 09/766,887

(22) Filed: Jan. 19, 2001

Related U.S. Application Data

(60) Provisional application No. 60/178,292, filed on Jan. 27, 2000.

(30) Foreign Application Priority Data

Jan. 21, 2000 (SE) ................................................ 0000178

(51) Int. Cl.[7] .......................... C07K 14/81; C07K 1/18; C12N 9/48; C12N 9/50
(52) U.S. Cl. ........................ 530/380; 530/416; 435/212; 435/219
(58) Field of Search ................................ 435/212, 219; 530/380, 416

(56) References Cited

U.S. PATENT DOCUMENTS 5,453,186 A * 9/1995 Muller et al.

FOREIGN PATENT DOCUMENTS

JP 07316072 A * 12/1995

OTHER PUBLICATIONS

Peterson et al. Isolation and characterization of an antithrombin III variant with reduced carbohydrate content and enhanced heparin binding (Jan. 10, 1985) J. Biol. Chem., vol. 260, No. 1, pp. 610–615.*

* cited by examiner

Primary Examiner—Jon P. Weber
(74) Attorney, Agent, or Firm—Sterne, Kessler, Goldstein & Fox P.L.L.C.

(57) ABSTRACT

PROTEIN PURIFICATION I

The invention relates to processes for preparation of substantially pure antithrombin-III (AT-III), the antithrombin isoforms AT-IIIα and AT-IIIβ; and/or histidine-rich glycoprotein (HRGP). The processes comprise separating the said proteins on a cation exchange gel wherein the cation exchanger group is attached to the gel matrix via a linear polymer chain.

20 Claims, 2 Drawing Sheets

1 2 3 4 5 6 7 8

1 2 3 4 5 6 7 8

PURIFICATION OF ANTITHROMBIN-III-α AND β

This application claims priority from Provisional application Ser. No. 60/178,292, filed Jan. 27, 2000.

TECHNICAL FIELD

The present invention relates to processes for the purification of the plasma glycoprotein antithrombin-III (AT-III). Particular aspects of the invention include methods for separation of the antithrombin isoforms AT-IIIα and AT-IIIβ, as well as methods for separating the AT-III isoforms from histidine-rich glycoprotein (HRGP).

BACKGROUND ART

Antithrombin III (AT-III) is a plasma glycoprotein that inhibits serine proteases in the coagulation cascade and thus plays a major role in the regulation of blood clotting. Antithrombin III is an inhibitor of Factors IX$a$, X$a$, XI, XII$a$, and thrombin. Thus, AT-III regulates clot formation in different stages of the coagulation cascade. A small decrease of the AT-III content in the blood is associated with increased risk of thromboembolism. AT-III concentrates are used in the prophylaxis and treatment of thromboembolic disorders in patients with acquired or hereditary antithrombin deficiency. In addition, it has been reported that AT-III is involved in many other biological responses, for example angiogenesis and inflammatory responses. The function of AT-III in these mechanisms is not yet fully understood.

Purification of AT-III with affinity chromatography, using heparin as the solid phase bound ligand, is known in the art. Miller-Andersson et al. (Thrombosis Research 5, 439–452, 1974) discloses the use of heparin-Sepharose to purify human AT-III. The entire procedure, which included ion exchange and gel filtration chromatography, provided a 34% yield.

In human plasma, antithrombin III exists as at least two molecular entities, which are homologous according to amino acid composition, but differ in carbohydrate content and in their heparin-binding behavior. An antithrombin variant, designated as AT-IIIβ, was isolated from human plasma independently from the predominant antithrombin species (designated as AT-IIIα), by virtue of its tight binding to a heparin-Sepharose matrix at high ionic strengths (Peterson, C. B. & Blackburn, M. N. (1985) J. Biol. Chem. 260, 610–615).

The determined molecular weights were 59,800 and 56,900 for human AT-IIIα and AT-IIIβ, respectively. The difference in molecular weights of the two antithrombins was attributed to a reduction of approximately 25–30% in the sialic acid, neutral sugar, and amino sugar content of AT-IIIβ when compared to the carbohydrate content of the AT-IIIα subspecies (Peterson & Blackburn, supra). It has been shown that AT-IIIβ lacks one of the four oligosaccharide side-chains, namely the side-chain at asparagine 135 (Brennan, S. O. et al. (1987) FEBS Letters 219, 431–436). The AT-IIIα form is more negatively charged than AT-IIIβ; it has been demonstrated that AT-IIIα and AT-IIIβ have pI:s of 4.9 and 5.1, respectively (Frebelius, S. et al. (1996) Arteriosclerosis, Thrombosis, and Vascular Biology 16:1292–1297).

It is desirable to obtain pure AT-IIIβ, as this form has specific effects on the coagulation in the vessel wall. It has been shown that AT-IIIβ can prevent restenosis of the rabbit aorta after balloon injury (Swedenborg (1998) Blood Coagulation and Fibrinolysis 9 (suppl. 3):S7–S10). AT-IIIβ may therefore be considered as a potential drug for humans in prophylaxis of restenosis when performing balloon dilatation of the aorta.

Histidine-rich glycoprotein (HRGP) is a single-chained plasma protein originally isolated in 1972. The exact physiological function of HRGP is still unknown. Due to interaction with heparin, fibrinogen and fibrin, plasminogen and activated platelets, HRGP is considered to be a modulator of coagulation and fibrinolysis (Koide, T. In: Fibrinolysis: Current Prospects. Gaffney, P J (Ed.), John Libbey & Co., London 1988, p.55–63). The polypeptide chain consists of 507 amino acid residues and contains regions that share homology with other plasma proteins, e.g. antithrombin-III (Koide, T. et al. (1986) Biochemistry 25, 2220–2225).

As indicated above, the complete involvement of the two AT-III isoforms and HRGP in the body is not yet fully understood. Consequently, it is desirable to provide efficient purification methods for producing the proteins in pure form which will facilitate studies in vivo and in vitro.

Figure 1A:
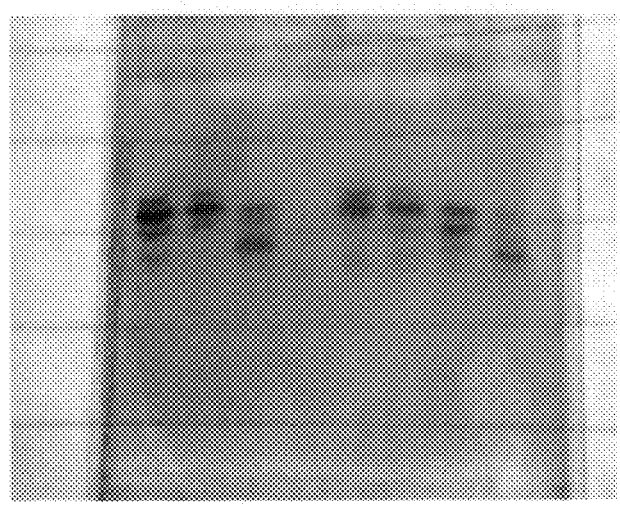
FIG. 1

Isoelectric focusing of protein samples collected during processes according to the invention (Example 1) or the process for comparison (Example 2).

Gel A
1 Concentrate UF1 (Example 1, step 2)
2 Fraction A1 (Example 1, step 2)
3 Fraction B1 (Example 1, step 2)
4 —
5 Fraction A2 (Example 1, step 3)
6 Wash fraction between A2 and B2 (Example 1, step 3)
7 Fraction B2 (Example 1, step 3)
8 Material eluted from the gel with 1 M NaCl (Example 1, step 3)

Gel B
1 Pooled fractions B1 and B2 (Example 1, step 4)
2 Material eluted under low ionic strength (Example 1, step 4)
3 Fraction B3 (first part of elution peak) (Example 1, step 4)
4 Fraction B3 (last part of elution peak) (Example 1, step 4)
5 Fraction A2 (Example 1, step 3)
6 Fraction B3 (Example 1, step 4)
7 Fraction D (Example 2)
8 Fraction D (Example 2)

FIG. 2

Comparison of chromatograms obtained from (A) purification of AT-IIIα by cation-change chromatography according to the invention (Fraction A2); and (B) purification of AT-IIIα by heparin-Sepharose chromatography according to known methods (Fraction D).

DISCLOSURE OF THE INVENTION

It has surprisingly been shown that a "tentacle" cation exchange gel, wherein the cation exchanger groups are attached to the gel matrix via a linear polymer chain, can advantageously be used for the separation of the antithrombin isoforms AT-IIIα and AT-IIIβ, as well as for the separation of histidine-rich glycoprotein (HRGP) from antithrombin. Such a cation exchange gel can conveniently be used for the purification, e.g. by column chromatography, of AT-III, AT-IIIα, AT-IIIβ and/or HRGP.

Consequently, in a first aspect this invention provides a process for the preparation of a solution comprising substantially pure antithrombin-Eff (AT-III), or an isoform thereof, said process comprising the use of a cation exchange gel wherein the cation exchanger group is attached to the gel matrix via a linear polymer chain.

In a preferred aspect, this invention provides a process for the preparation of a solution comprising substantially pure antithrombin-III (AT-III), comprising the steps
(i) preparing a solution mainly comprising AT-III and histidine-rich glycoprotein (HRGP);
(ii) contacting the said solution with a cation exchange gel wherein the cation exchanger group is attached to the gel matrix via a linear polymer chain, under conditions where AT-III can be eluted from the gel under low ionic strength, while HRGP is attaching to the gel under low ionic strength; and
(iii) eluting, under low ionic strength conditions, and collecting a protein fraction, thereby obtaining a solution comprising substantially pure AT-III.

The said solution mainly comprising AT-III and histidine-rich glycoprotein (HRGP) can conveniently be prepared according methods known in the art. A suitable method could e.g. include the steps:
(i) preparing a Cohn Fraction I supernatant from human plasma by known methods (see e.g. Cohn et al. (1946) J. Am. Chem. Soc. 68, 459–475)
(ii) contacting the said Cohn Fraction I supernatant with an affinity gel capable of binding AT-III and HRGP (see e.g. Koide, T. et al. (1985) J. Biochem. 98, 1191–1200); and
(iii) eluting and collecting the protein fraction binding to the said affinity matrix.

The said affinity gel preferably comprises heparin as the affinity ligand. Suitable affinity gels include heparin-Sepharose® (Amersham Pharmacia); HeparinHyperD (Biosepra), Fractogel TSK AF-Heparin 650 (Merck), Heparin-Agarose (Sigma), TSKgel Heparin (Tosohaas), Heparin-Agarose 6XL (ACL).

The said cation exchange step is carried out by adsorption chromatography, preferably column chromatography. In ion exchange chromatography, charged substances are separated via column materials that carry an opposite charge (see e.g. Scopes, R. K. Protein Purification, Principles and Practice, Third edition, Springer-Verlag 1993). The ionic groups of exchanger columns are covalently bound to the gel matrix and are compensated by small concentrations of counter ions, which are present in the buffer. When a sample is added to the column, an exchange with the weakly bound counter ions takes place.

As well known by the skilled person, chromatography uses the fact that proteins are multivalent anions or cations. Due to the total charge (net charge) of the proteins it is possible to bind them to a charged stationary phase, as long as the salt concentration is kept low. Salt gradients are the most common means of eluting proteins from ion exchangers. Excessively high salt concentrations cause shielding of the charges on the protein surface and effective binding to an exchanger can no longer take place. Since the bound proteins are subsequently displaced with the aid of an increasing salt gradient, proteins varying in charge can be separated. The action of the salts can be considered in one of two ways. The salt can directly displace the protein; the ions occupy the charged sites and block reattachment by protein. Alternatively, the system can be regarded as an equilibrium in which even strongly bound proteins spend some time not adsorbed; the presence of the salt ions between the unattached protein and the adsorbent weakens the attraction between the two. In either case, the desorbed proteins are replaced by counter-ions. Elution of proteins can be carried by stepwise higher salt concentrations, or by linear or non-linear salt gradients.

As mentioned above, the cation exchange gel to be used according to the invention comprises a linear polymer chain, grafted on the support surface, serving as a spacer or "tentacle" enabling the functional ionic groups to adopt a configuration that is optimal for their interaction with the protein during chromatography. Such "tentacle" ion exchangers have been described e.g. by Müller, W. (1990) J. Cromatography 510, 133–140; Ditz, R. et al. (1991) Australian J. Biotechnol. 5, 101–102; and Donovan, J. et al. (1991) Am. Biotechnol. Lab. 9, 20–22.

Suitable "linear polymer chains" include in particular those included in the separating materials disclosed in U.S. Pat. No. 5,453,186 (Müller et al.). The said patent discloses a separating material comprising a primary or secondary aliphatic hydroxyl group-containing support coated with at least one covalently bonded polymer, wherein
(1) the covalently bonded polymers are bonded to the support by graft polymerization via the α-carbon atoms of the hydroxyl groups, and
(2) the polymer contains identical or different recurring units of the formula

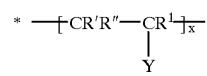

wherein $R^1$ is H or $CH_3$;
Y is

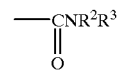

or

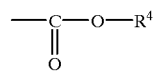

R' and R" are each independently H or $CH_3$,
$R^2$ and $R^3$ are each independently
(a) $C_{1-10}$-alkyl, phenyl, phenyl-$C_{1-10}$-alkyl, cycloalkyl, $C_{1-10}$-alkyl-cycloalkyl or $C_{1-10}$-alkylphenyl,
(b) one of the above groups in (a) monosubstituted or polysubstituted by each of amino, mono- or dialkylamino, trialkylammonium, carboxyl, or sulfonyl,
(c) a cyclic or bicyclic radical having 5–10 C atoms, wherein one or more CH or $CH_2$ groups is replaced by (i) N or NH, (ii) N or NH and S, or (iii) N or NH and O, or
(d) one of $R^2$ or $R^3$ is H; and wherein $R^2$ and $R^3$ are coordinated with one another so that either both radicals are acidic or basic, or one of the radicals is neutral and one is acidic or basic,
x is 2 to 100,
and $R^4$ is $C_{1-10}$-alkyl, phenyl, phenyl-$C_{1-10}$-alkyl, cycloalkyl or $C_{1-10}$-alkyl-cycloalkyl, or $C_{1-10}$-cyclophenyl, each monosubstituted or polysubstituted by carboxyl or sulfonyl.

For the purpose of the present invention, particularly preferred separating materials include those described in U.S. Pat. No. 5,453,186 wherein R' and R" are H, R$^1$ is H, and Y is

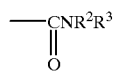

wherein R$^2$ is H, and R$^3$ is C$_{1-10}$-alkyl, e.g. isobutyl, substituted with a functional group, e.g. sulfonyl. Consequently, the said linear polymer chain preferably consists of recurring units of the formula

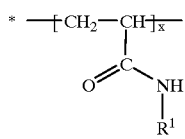

wherein x is 2 to 100; and R$^1$ is branched or unbranched C$_{1-10}$-alkyl, e.g. isobutyl, said alkyl being substituted with a strong acidic ion exchange group, such as sulfonyl.

In a preferred embodiment of the present invention, the said cation exchanger is a strongly acidic cation exchanger, having e.g. a sulfonic group as its functional group. Other possible functional groups include carboxymethyl (CM). A preferred cation exchange gel is Fractogel® EMD SO3-650 (M) (Merck, Darmstadt, Germany) wherein the functional sulfonic group is coupled to the gel matrix via a hydrophobic "tentacle" spacer arm comprising sulfoisobutylacrylamide units. The medium length of the polymer chains is 15 to 50 monomer units, carrying the same number of side chain ligands.

As shown in Example 1, Step 2, below, AT-III can be conveniently separated from HRGP, and thus purified, by the method as defined above. In a further aspect, this method includes the separation and purification of the AT-III isoforms AT-IIIα and AT-IIIβ. A protein solution mainly comprising AT-IIIα can be obtained by collecting a protein fraction, which is the earlier of two main protein fractions eluting from the gel under low ionic strength conditions. A protein solution mainly comprising AT-III can be obtained by collecting a protein fraction, which is the later of two main protein fractions eluting from the gel under low ionic strength conditions. In the Example below, retention times of 8 and 104 min for AT-IIIα and AT-IIIβ, respectively, have been shown. However, the skilled person will understand that the retention time will depend on a number of factors, such as the pH and ionic strength of the elution buffer, temperature, column dimensions, protein load, and flow rate. General information on the effect of various parameters can be found in textbooks on protein purification, such as the one by Scopes (supra).

In the present context, the term "low ionic strength conditions" implies using an elution buffer having a conductivity at room temperature of rom about 0.1 to about 6 mS/cm, preferably from about 1 to about 4 mS/cm, and more preferably from about 2 to about 3 mS/cm, such as about 2.6 mS/cm. A suitable buffer could comprise e.g. sodium citrate sodium acetate, sodium phosphate, Tris(base) or potassium phosphate, alone or in combination with other salts such as sodium chloride, at a concentration from about 1 to about 20 mM, such as about 10 mM. The cation exchange step is preferably carried out at neutral pH, more specifically at a pH from about 6.5 to about 8, preferably around 7.5.

In a further aspect, this invention provides a process for the preparation of a solution comprising substantially pure histidine-rich glycoprotein (HRGP) comprising eluting, under medium or high ionic strength conditions, and collecting the protein fraction attaching to the cation exchange gel during the step (ii) as defined above. The elution of HRGP is preferably carried out at the same pH as used during elution of AT-III.

For the purpose of the present description, the term "medium ionic strength conditions" implies using an elution buffer having a conductivity at room temperature of from about 4 to about 16 mS/cm. The term "high ionic strength conditions" implies using an elution buffer having a conductivity at room temperature of from about 10 to about 450 mS/cm. In both cases, a suitable buffer could comprise e.g. sodium citrate sodium acetate, sodium phosphate, Tris(base) or potassium phosphate, alone or in combination with other salts such as sodium chloride, at a concentration from about 1 mM to about 2 M.

For eluting the protein fraction comprising HRGP, the term "medium or high ionic strength conditions" thus implies using an elution buffer having a conductivity at room temperature of from about 4 to about 450 mS/cm, or from about 10 to about 450 mS/cm, preferably from about 50 to about 150 mS/cm, and more preferably from about 80 to about 110 mS/cm, such as about 106 mS/cm. As shown in Example 1, step 2, below, HRGP could be eluted with a buffer comprising 10 mM sodium citrate and 1 M NaCl.

In yet another aspect, this invention provides a process for the preparation of a solution comprising a purified isoform of AT-III, comprising the steps (i) preparing a solution comprising purified or substantially pure AT-III;

(ii) contacting the said protein solution with a cation exchange gel wherein the cation exchanger group is attached to the gel matrix via a linear polymer chain, under conditions where AT-IIIα can be eluted from the gel under low ionic strength, while AT-IIIβ is attaching to the gel under low ionic strength conditions; and (iii) eluting, under low ionic strength conditions, and collecting a protein fraction, thereby obtaining a solution comprising substantially pure AT-IIIα; and/or (iv) eluting, under medium or high ionic strength conditions, and collecting a protein fraction, thereby obtaining a solution comprising AT-IIIβ.

The starting material, i.e. the solution comprising purified AT-III, could advantageously be a solution comprising substantially pure AT-III, prepared according to the invention as described above. The cation exchange step is preferably carried out at a pH from about 6.5 to about 7.25, more preferably around 6.75.

The terms "low ionic strength conditions", "medium ionic strength conditions" and "high ionic strength conditions" are defined above. For eluting the protein fraction comprising AT-IIIβ, the term "medium or high ionic strength conditions" thus implies using an elution buffer having a conductivity at room temperature of from about 4 to about 450 mS/cm, preferably from about 4 to about 30 mS/cm, and more preferably from about 4 to about 16 mS/cm; or from about 10 to about 16 mS/cm, such as about 13 mS/cm. As shown in Example 1, step 3, below, AT-IIIβ could be eluted with a buffer comprising 10 mM sodium citrate and 0.15 M NaCl.

In yet a further aspect, the invention provides a process for the preparation of a solution comprising substantially pure AT-IIIβ, comprising the steps (i) preparing, according to any one (alone or in combination) of the methods of the invention as described above, a solution comprising AT-IIIβ;

(ii) contacting the said solution with a cation exchange gel wherein the cation exchanger group is attached to the gel matrix via a linear polymer chain, under conditions where AT-IIIα can be eluted from the gel under low or medium ionic strength, while AT-IIIβ is attaching to the gel under low or medium ionic strength; and (iii) eluting, under low and/or medium ionic strength conditions, a protein fraction, thereby eluting AT-IIIα from the column; and (iv) eluting, under high ionic strength conditions, and collecting a protein fraction, thereby obtaining a solution comprising AT-IIIβ.

The cation exchange step is preferably carried out at a pH from about 6.75 to about 7.25, more preferably around 7.0.

It will be understood by the skilled person that the starting solution may have to be treated in a suitable manner before contacting the said solution with a cation exchange gel. It is normal for the applied protein mixture to be in the same buffer used to equilibrate the column. Further, the pH and ionic strength should be similar or identical with the column buffer. There are two usual ways of attaining the correct buffer composition: dialysis or gel filtration (see e.g. Scopes, R. K. Protein Purification, Principles and Practice, Third edition, Springer-Verlag 1993). Alternatively, a suitable conductivity can be attained by dilution with distilled water, as in Example 1, step 4, below. A suitable pH value can be obtained by addition of a base such as sodium hydroxide or an acid such as citric acid.

The terms "low ionic strength conditions", "medium ionic strength conditions" and "high ionic strength conditions" are defined above. For eluting the protein fraction comprising AT-IIIα, the term "medium ionic strength conditions" implies using an elution buffer having a conductivity at room temperature of from about 4 to about 16 mS/cm, preferably from about 5 to about 10 mS/cm, such as about 7 mS/cm. As shown in Example 1, step 4, below, trace amounts of AT-IIIα can be eluted with a buffer comprising 10 mM sodium citrate and, optionally, 0.08 M NaCl in order to subsequently obtain pure AT-IIIβ.

For eluting the protein fraction comprising AT-IIIβ, the term "high ionic strength conditions" implies using an elution buffer having a conductivity at room temperature of approximately 10 to 450 mS/cm , preferably 50 to 150 mS/cm, and more preferably 80 to 110 mS/cm, such as around 106 mS/cm. As shown in Example 1, step 4, below, AT-IIIβ could be eluted with a buffer comprising 10 mM sodium citrate and 1 M NaCl.

The antithrombin preparations produced according to the present invention are suitable as pharmaceutically effective ingredients in pharmaceutical compositions and combinations. The pharmaceutical compositions may optionally comprise additional active ingredients like anti-coagulants such as hirudin or heparin ,or thrombolytic agents such as plasminogen activator or hementin. The antithrombin preparations produced according to the invention may form pharmaceutically acceptable salts with any non-toxic, organic or inorganic acid.

The antithrombin preparations produced according to the invention may be administered as unit doses containing conventional non-toxic pharmaceutically acceptable carriers, diluents, adjuvants and vehicles which are typical for parenteral administration. As used herein, the term "pharmaceutically acceptable carrier" means an inert, non toxic solid or liquid filler, diluent or encapsulating material, not reacting adversely with the active compound or with the patient. Suitable, preferably liquid carriers are well known in the art such as sterile water, saline, aqueous dextrose, sugar solutions, ethanol, glycols and oils, including those of petroleum, animal, vegetable, or synthetic origin, for example, peanut oil, soybean oil and mineral oil.

The term "parenteral" includes herein subcutaneous, intravenous, intra-articular and intratracheal injection and infusion techniques. Also other administrations such as oral administration and topical application are suitable. Parenteral compositions and combinations are most preferably administered intravenously either in a bolus form or as a constant fusion according to known procedures. Tablets and capsules for oral administration contain conventional excipients such as binding agents, fillers, diluents, tableting agents, lubricants, disintegrants, and wetting agents. The tablets may be coated according to methods well known in the art.

Oral liquid preparations may be in the form of aqueous or oily suspensions, solutions, emulsions, syrups or elixirs, or may be presented as a dry product for reconstitution with water or another suitable vehicle before use. Such liquid preparations may contain conventional additives like suspending agents, emulsifying agents, non-aqueous vehicles and preservatives. Topical applications may be in the form of aqueous or oily suspensions, solutions, emulsions, jellies or preferably emulsion ointments.

Unit doses according to the invention may contain daily required amounts of the protein according to the invention, or sub-multiples thereof to make up the desired dose. The optimum therapeutically acceptable dosage and dose rate for a given patient (mammals, including humans) depends on a variety of factors, such as the activity of the specific active material employed, the age, body weight, general health, sex, diet, time and route of administration, rate of clearance. The object of the treatment, i.e., therapy or prophylaxis and the nature of the thrombotic disease to be treated, antiplatelet or anticoagulant activity.

In compositions and combinations useful as anticoagulants in a treated patient (in vivo) a pharmaceutical effective daily dose of the peptides of this invention is between about 0.01 and 100 mg/kg body weight, preferably between 0.1 and 10 mg/kg body weight .

EXPERIMENTAL METHODS

Biological activity (IU/ml) of AT-III was determined as heparin cofactor activity by monitoring the cleavage of the chromogenic substrate H-D-Phe-Pip-Arg-pNA.2 HCl (Chromogenix, Sweden) by thrombin in presence of heparin and AT-III. See Frantzen Handeland et al. (Scand. J. Haematol. 31, 427–436, 1983) and van Voorhuizen et al. (Thromb. Haemostas. 52(3), 350–353, 1984).

Total protein concentration was determined by absorption measurements at 280 nm ($A_{280}$). Concentration (mg/ml) for AT-III solutions was calculated using the coefficient of 6.4 IU/mg. Specific activity (SA) of AT-III was defined as the ratio between heparin cofactor activity calculated as IU/ml and $A_{280}$.

HRGP was quantitated using rocket electrophoresis technique wherein the height of the "rocket" is proportional to the antigen concentration (Laurell, C-B, (1966) Analyt. Biochem. vol. 15, p. 45; and Laurell, C-B (1972) J. Clin. Lab. Invest. vol. 29, suppl. 124, p. 21). HRGP rabbit antibodies (Behringewerke) was included in a 1% Agarose A gel (Amersham Pharmacia Biotech). HRGP sample (5 μl) was applied to the gel, which was run over night (150 V, 1 V/cm). The resulting antibody-antigen complex was stained and compared to the standard (human serum).

Isoelectric focusing was carried out using the PhastSystem (Amersham Pharmacia Biotech) with precast gels, pI 3–9, according to the Phast manual separation technique file No.100.

The strongly acidic cation exchange gel Fractogel® EMD SO3-650 (M) was purchased from Merck, Darmstadt, Germany (Catalogue No. 1.16882). The functional sulfonic groups of the gel, $SO_3$-, are coupled to the gel matrix via hydrophobic "tentacle" spacer arms. The monomer structure of the ligand (functional group and spacer arm in combination) is, more specifically, sulfoisobutylacrylamide.

Protein samples were characterized for AT-IIIα, AT-IIIβ and HRGP using a 10 ml Fractogel® EMD SO3-650 (M) column. The gel was equilibrated with 10 mM sodium citrate, pH 7.5, Protein sample (50 µl) was applied to the gel and the column was washed with 3 volumes of equilibration buffer (1 ml/min). The proteins which adsorbed to the column were eluted with 1 M sodium chloride /10 mM sodium citrate, pH 7.5. Protein peaks were detected at 280 nm.

EXAMPLES

Example 1: Separation of AT-IIIα, AT-IIIβ and HRGP according to the invention Step 1

Blood plasma (1200 kg) was thawed at 0° C. and the resulting cryoprecipitate (comprising e.g. factor VIII and fibronectin) was removed through centrifugation. The resulting cryosupernatant was processed through an anion exchange column (70 liter DEAE-Sepharose FF, Amersham Pharmacia Biotech) to bind vitamin K-dependent proteins (factor IX, factor X, factor II, Protein C, Protein S, etc.). The buffer contained 0.14 M sodium chloride and 5 mM sodium phosphate, pH 7.0. The protein fraction which did not bind to the column was further processed by addition of ethanol to a final concentration of 8% (v/v). The obtained Cohn Fraction 1 precipitate (comprising e.g. fibrinogen and lipoproteins, see Cohn et al. (1946) J. Am. Chem. Soc. 68, 459–475) was removed by centrifugation.

The Cohn Fraction 1 supernatant (1400 kg) was processed through an affinity chromatography column (120 liter heparin-Sepharose FF, Amersham Pharmacia Biotech) whereby antithrombin and HRGP (histidine-rich glycoprotein) bound, while the main part of other plasma proteins passed through the column. The column was washed with 600 kg buffer (0.4 M sodium chloride and 0.01 M sodium phosphate, pH 7.8), and the antithrombin/HRGP fraction was eluted with 500 kg buffer (2.3 M NaCl and 0.01 M sodium phosphate, pH 7.8). The resulting antithrombin-rich eluate was concentrated and diafiltrated against 0.05 M sodium phosphate, pH 7.5, using an ultrafiltration membrane (Biomax-10, Millipore). The obtained diafiltrated concentrate was designated as UF1.

Step 2

Steps 2 through 4 were carried out at room temperature (+22° C.). The concentrate UF1 ($A_{280}$=23.6; FIG. 1A, lane 1) was diluted 1+3 with distilled water. The diluted solution (2050 g, conductivity 2.6 mS/cm) was processed through a column (Pharmacia Biotech Bioprocess Column, 15 cm diameter) filled with Fractogel® EMD SO3-650 (M) cation-exchange chromatography media (1.7 l) equilibrated with 10 mM sodium citrate, pH 7.5, 2.6 mS/cm. The flow rate was 9 l/h. When the protein solution had been loaded on the column, the column was washed with 7 volumes of equilibration buffer. The material that did not adsorb to the column (designated as "Fraction A1"; FIG. 1A, lane 2) was collected (retention time 8 min; 2.3 kg) and further processed in Step 3, below. The material, which was retarded by the cation exchanger and collected throughout the wash (designated as "Fraction B1"; FIG. 1A, lane 3), was collected (retention time 104 min; 13.3 kg) and further processed in Step 4, below.

The more strongly adsorbed proteins were eluted from the column with 1.9 kg buffer (1 M NaCl/10 mM sodium citrate, pH 7.5, conductivity 106 mS/cm). The eluate (1.9 kg) was concentrated and diafiltered against 0.1 M sodium citrate/ 1% saccharose, pH 7.0. The obtained "Fraction C" contained essentially pure HRGP (Table I).

Step 3

Figure 1B:
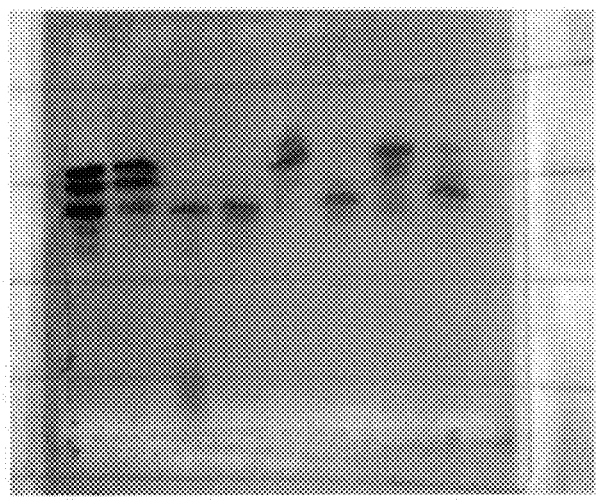

Fraction A1 obtained in Step 2 was adjusted with 1 M citric acid to a pH of 6.75. The solution (2.3 l, conductivity 2.6 mS/cm) was processed through the same column as in Step 2 (1.7 liter Fractogel® EMD SO3-650 (M)). The gel was equilibrated with 10 mM sodium citrate, 2.6 mS/cm, pH 6.75. The flow rate was 9 l/h. After the protein solution (2.3 l) had been pumped on the column, the column was washed with 3 volumes of equilibration buffer. Proteins which did not adsorb to the column were collected (2.5 l), concentrated and diafiltered against 0.1 M sodium citrate/1% saccharose, pH 7.0. The obtained "Fraction A2" contained essentially pure AT-IIIα (Table I; FIG. 1A, lane 5; FIG. 1B, lane 5; and FIG. 2A). A second fraction (FIG. 1A, lane 6), eluted from the column with equilibration buffer, was discarded in order to minimize contamination in the AT-IIIα fraction.

Proteins which were more strongly adsorbed by the column was washed out under "medium" ionic strength with 3 column volumes of 0.15 M NaCl/10 mM sodium citrate buffer (conductivity approximately 13 mS/cm, pH 6.75), collected (5 l, "Fraction B2"; FIG. 1A, lane 7) and further processed in Step 4.

Step 4

The fractions designated as B1 and B2 were pooled (FIG. 1B, lane 1) and pH was adjusted to 7.0. Distilled water was added until a conductivity of 2.6 mS/cm was reached. The solution (40.6 l) was then processed through the same column as in Steps 2 and 3 (1.7 liter Fractogel® EME SO3-650 (M)), equilibrated with 10 mM sodium citrate, 2.6 mS/cm, pH 7.0. The flow rate was 2 l/h. To remove trace amounts of AT-IIIα, the column was washed with 1 volume of equilibration buffer (2.6 mS/cm) (see FIG. 1B, lane 2) and subsequently with 1 volume of 80 mM NaCl/10 mM sodium citrate buffer (7 mS/cm, pH 7.0). The AT-IIIβ fraction was then eluted with 3 column volumes of 1 M NaCl/10 mM sodium citrate, pH 7.0, 106 mS/cm (retention time 52 min). The eluted material (2 liters) was concentrated and diafiltered against 0.1 M sodium citrate/1% saccharose, pH 7.0. The obtained "Fraction B3" (FIG. 1B, lanes 4 and 6) contained essentially pure AT-IIIβ (Table I).

TABLE I

Separation of AT-IIIα, AT-IIIβ and HRGP fractions according to the invention

| | $A_{280}$ | AT-III (IU/ml) | AT-III SA | AT-III (%) | AT-IIIα (%) | HRGP (mg/ml) |
|---|---|---|---|---|---|---|
| UF1 | 33 | 341 | 10 | >80 | >90 | N.D. |
| Fraction A2 (AT-IIIα) | 45 | 500 | 11 | >95 | >95 | <0.01 |
| Fraction B3 (AT-IIIβ) | 4.5 | 44 | 10 | >95 | <5 | <0.01 |
| Fraction C (HRGP) | 16 | 2 | 0.1 | <1 | <1 | 4.2 |

In Tables I and II, the column "AT-III (%)" is an estimate of the purity of AT-III (AT-IIIα and AT-IIIβ) in per cent of the total protein content, while "AT-IIIα (%)" is an estimate of the purity of AT-IIIα in percent of the total AT-III content. In both cases the values are estimated from observations from isoelectric focusing and analytical cation exchange chromatography.

In similar experiments with other types of cation exchanger (CM-Sepharose®, SP-Sepharose®, Fractogel® CM-650 (M); where CM denotes carboxymethyl and SP denotes sulfopropyl) a sufficient separation of AT-IIIα, AT-IIIβ and HRGP was not achieved. It is concluded that the higher exchange capacity of the media provided with a "tentacle" spacer arm is necessary for efficient separation of AT-IIIα, AT-IIIβ and HRGP.

Example 2: Separating AT-III(X and AT-IIIl in a known way using heparin-Sepharose chromatography Heparin-Sepharose FF gel (13 l) was poured into a column (d=32 cm) and equilibrated with 0.15 M NaCl/20 mM Tris, pH 7.5. The concentrate designated as UF1 (see Example 1, Step 1) (7075 g; heparin cofactor activity 78 IU/ml) was applied to the gel. The flow was 50 l/h. The column was washed with 3 volumes of equilibration buffer and elution was started with a linear gradient (10 column volumes) from 0.15 to 1.5 M NaCl. Protein elution was followed using a flow-through spectrophotometer (280 nm). The first protein peak, about 60 liters, was collected and concentrated on a ultrafiltration system (PLGC 10kd, Millipore). The obtained "Fraction D" contained mainly AT-IIIα (Table II; and FIG. 1B, lane 7). The second peak, about 100 liters, was collected and concentrated on an ultrafiltration system (PLGC 10kd, Millipore). The obtained "Fraction E" contained AT-IIIβ (Table II; and FIG. 1B, lane 8).

TABLE II

Separation of AT-IIIα, and AT-IIIβ fractions according to known methods

|  | $A_{280}$ | AT-III (IU/ml) | AT-III SA | AT-III (%) | AT-IIIα (%) | HRGP (mg/ml) |
|---|---|---|---|---|---|---|
| UF1 | 7.1 | 78 | 11 | >80 | >95 | N.D. |
| Fraction D (AT-IIIα) | 8.6 | 67 | 8 | >60 | >90 | 1.9 |
| Fraction E (AT-IIIβ) | 5.3 | 48 | 9 | >80 | 10–30 | 0.9 |

A comparison of Tables I and II indicates that the method according to the invention (Example 1) is superior for the purification of AT-IIIα and AT-IIIβ. The AT-IIIα fraction (A2) from Example 1 contained less than 5% of AT-III and less than 5% of HRGP, while the AT-IIIα fraction (D) from Example 2 contained more than one third of HRGP as well as a higher amount of AT-IIIβ. The AT-IIIβ fraction (B3) from Example 1 contained less than 5% of AT-IIIα and less than 5% of HRGP, while the AT-IIIβ fraction (E) from Example 2 was contaminated with HRGP (about 20%) as well as AT-IIIα (10–30%).

The results obtained with isoelectric focusing (FIG. 1) confirm that the method according to the invention is superior over the known method. Lanes 5 and 6 in FIG. 1B show fractions A2 and B3, respectively, obtained according to the invention. Lanes 7 and 8 in FIG. 1B show fractions D and E obtained according to the known method of Example 2. Two distinct bands for each of AT-IIIα (Lane 5) and AT-IIIβ (Lane 6) are visible. In contrast, lanes 7 and 8 indicate cross-contamination of the two AT-III isoforms. The same amount of protein has been applied in lanes 5 to 8.

Figures 2A, 2B:
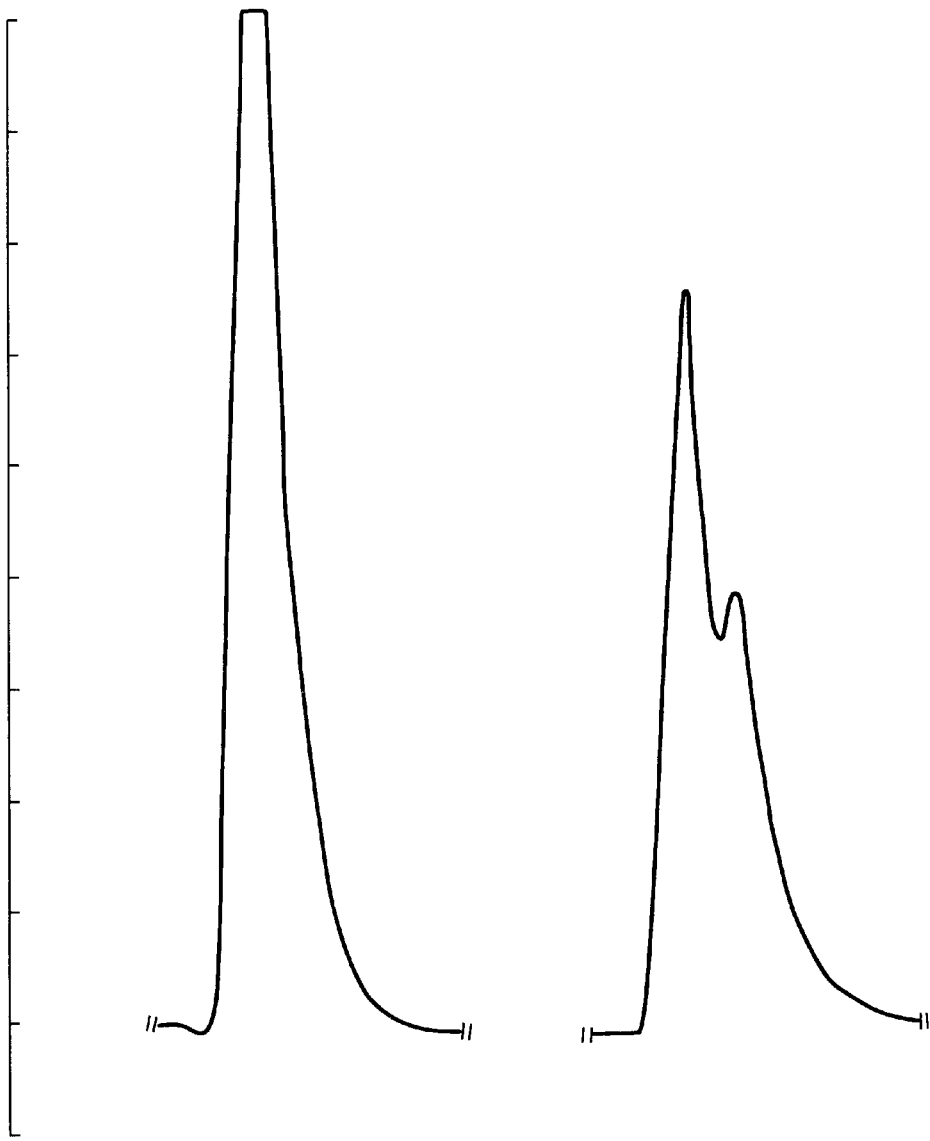

The difference of the methods according to Example 1 and Example 2 is also evident from FIG. 2. The sample of AT-III60 purified according to the invention (Fraction A2, FIG. 2A) is represented by a single peak, while the peak representing Fraction D (FIG. 2B) indicates contamination of other proteins. A similar result was obtained with a comparison between fractions B3 and E.

What is claimed is:

1. A process for the preparation of a solution comprising substantially pure antithrombin-III (AT-III) an -α or -β isoform, said process comprising contacting a solution of AT-III-α and -β with a cation exchange gel wherein the cation exchanger groups are attached to the gel matrix via a linear polymer chain, and recovering the AT-III-α or -β.

2. A process according to claim 1 for the preparation of a solution comprising substantially pure AT-III-α or -β, comprising the steps
    (i) preparing a solution comprising AT-III-α and β and histidine-rich glycoprotein (HRGP);
    (ii) contacting the said solution with a cation exchange gel wherein the cation exchanger group is attached to the gel matrix via a linear polymer chain, under conditions where AT-III-α or -β can be eluted from gel under low ionic strength of from 1–4 mS/cm, while HRGP remains attached to the gel under said low ionic strength; and
    (iii) eluting, under said low ionic strength conditions, and collecting a protein fraction, thereby obtaining a solution comprising substantially pure AT-III-α or -β.

3. The process according to claim 2 wherein the cation exchange step is carried out by column chromatography.

4. The process according to claim 3, wherein step (iii) comprises collecting a protein fraction which is the early of the two main protein fractions eluting from the gel under said low ionic strength conditions, thereby obtaining a protein solution comprising AT-IIIα.

5. The process according to claim 3, wherein step (iii) comprises collecting a protein fraction which is the later of the two main protein fractions eluting from the gel under said low ionic strength conditions, thereby obtaining a protein solution comprising AT-IIIβ.

6. The process according to claim 2 wherein AT-III is eluted from the cation exchange gel with a buffer having a conductivity of 2–3 mS/cm at room temperature.

7. The process according to claim 2 wherein the cation exchange step is carried out at a pH from 6.5 to 8.

8. The process according to claim 2 wherein the said solution comprising AT-III-α and -β and HRGP is prepared by a process comprising the step
    (i) preparing a Cohn Fraction I supernatant from human plasma;
    (ii) contacting the said Cohn Fraction I supernatant with an affinity gel capable of binding AT-III-α and -β and HRGP; and
    (iii) eluting and collecting the protein fraction binding to the said affinity matrix.

9. The process according to claim 8 wherein-the said affinity gel comprises heparin as the affinity ligand.

10. A process according to claim 1 for the preparation of a solution comprising substantially pure AT-IIIβ, comprising the steps
    (i) preparing a solution comprising AT-III-α and β and histidine-rich glycoprotein;
    (ii) contacting the said solution with a cation exchange gel in a chromatography wherein the cation exchanger group is attached to the gel matrix via a linear polymer chain, under conditions where AT-IIIα can be eluted from the gel under low or medium ionic strength of from 1–4 mS/cm, while AT-IIIβ remains attached to the gel under said low or medium ionic strength;

(iii) eluting, under said low or medium ionic strength conditions, a protein fraction; and (iv) eluting, under high ionic strength conditions of from 10 –450 mS/cm, and collecting a protein fraction, thereby obtaining a solution comprising AT-IIIβ.

11. The process according to claim 10 wherein AT-IIIβ is eluted from the cation exchange gel with a buffer having a conductivity of 50–150 mS/cm at room temperature.

12. The process according to claim 10 wherein the cation exchange step is carried out at a pH from 6.75 to 7.25.

13. The process according to claim 1 wherein said cation exchanger is a strongly acidic cation exchanger.

14. The process according to claim 13 wherein the said strongly acidic cation exchanger has a sulfonic group as its functional group.

15. The process according to claim 14 wherein the said linear polymer chain consists of recurring units of the formula

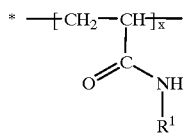

wherein x is 2 to 100; and

R$^1$ is branched or unbranched C$_{1-10}$-alkyl, substituted with sulfonyl.

16. The process according to claim 15 wherein the said C$_{1-10}$-alkyl is isobutyl.

17. A process for the preparation of a solution comprising a purified isoform -α or -β of AT-III, comprising the steps (i) preparing a solution comprising substantially pure AT-III-α and -β;

(ii) contacting the said protein solution with a cation exchange gel wherein the cation exchanger group is attached to the gel matrix via a linear polymer chain, under conditions where AT-IIIα can be eluted from the gel under low ionic strength of from 1–4 S/cm, while AT-IIIβ remains attached to the gel under said low ionic strength conditions;

(iii) eluting, under said low ionic strength conditions, and collecting a protein fraction, thereby obtaining a solution comprising substantially pure AT-IIIα; and (iv) eluting, under medium or high ionic strength conditions of from 10–450 mS/cm, and collecting a protein fraction, thereby obtaining a solution comprising AT-IIIβ.

18. The process according to claim 17 wherein AT-IIIα is eluted from the cation exchange gel with a buffer having a conductivity of 2–3 mS/cm at room temperature.

19. The process according to claim 17 wherein AT-IIIβ is eluted from the cation exchange gel with a buffer having a conductivity of 50–150 mS/cm at room temperature.

20. The process according to claim 17 wherein the cation exchange step is carried out at a pH from 6.5 to 7.25.

* * * * *

UNITED STATES PATENT AND TRADEMARK OFFICE
CERTIFICATE OF CORRECTION

PATENT NO. : 6,451,978 B2
DATED : September 17, 2002
INVENTOR(S) : Winge

It is certified that error appears in the above-identified patent and that said Letters Patent is hereby corrected as shown below:

<u>Column 12,</u>
Line 7, please delete "(AT-III) an -α" and insert therein -- (AT-III) -α --.

Signed and Sealed this

Third Day of June, 2003

JAMES E. ROGAN
*Director of the United States Patent and Trademark Office*